United States Patent
Roy et al.

(10) Patent No.: US 10,424,410 B2
(45) Date of Patent: Sep. 24, 2019

(54) TIERED TIME-IN-RANGE GUIDING INTERFACES FOR DIABETES MANAGEMENT

(71) Applicant: Verily Life Sciences LLC, Mountain View, CA (US)

(72) Inventors: Nikhil Roy, Sunnyvale, CA (US); Howard Zisser, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 15/809,944

(22) Filed: Nov. 10, 2017

(65) Prior Publication Data

US 2019/0147139 A1    May 16, 2019

(51) Int. Cl.
| | |
|---|---|
| *A61B 5/00* | (2006.01) |
| *G16H 40/63* | (2018.01) |
| *A61B 5/145* | (2006.01) |
| *G16H 10/60* | (2018.01) |

(52) U.S. Cl.
CPC .......... *G16H 40/63* (2018.01); *A61B 5/0002* (2013.01); *A61B 5/14532* (2013.01); *A61B 5/7282* (2013.01); *A61B 5/743* (2013.01); *A61B 5/7475* (2013.01); *G16H 10/60* (2018.01); *A61B 5/4842* (2013.01); *A61B 5/7275* (2013.01); *A61B 5/746* (2013.01)

(58) Field of Classification Search
CPC .... G16H 40/63; G16H 10/60; G06F 19/3406; G06F 19/322; A61B 5/743; A61B 5/7282; A61B 5/0002; A61B 5/7475; A61B 5/14532; A61B 5/746; A61B 5/7275; A61B 5/4842
See application file for complete search history.

(56) References Cited

U.S. PATENT DOCUMENTS

| | | | |
|---|---|---|---|
| 2008/0162182 A1* | 7/2008 | Cazares | ................. G06Q 50/22 705/2 |
| 2009/0054753 A1* | 2/2009 | Robinson | ........... A61B 5/14503 600/365 |
| 2014/0039383 A1* | 2/2014 | Dobbles | .............. A61M 15/008 604/66 |

(Continued)

FOREIGN PATENT DOCUMENTS

WO    2014145335 A1    9/2014

*Primary Examiner* — Navin Natnithithadha
*Assistant Examiner* — Andrey Shostak
(74) *Attorney, Agent, or Firm* — Perkins Coie LLP

(57) ABSTRACT

Introduced here are diabetes management platforms able to guide people with diabetes toward a glycemic target. Rather than state the absolute amount of glucose within the blood, the diabetes management platform can instead produce personalized glycemic goals based on the physiological data associated with an individual. For example, if the diabetes management platform determines that the time spent within a first glycemic range exceeds a specified threshold, then the diabetes management platform may recommend that the individual attempt to keep their blood glucose level within a second glycemic range. Generally, the second glycemic range is closer than the first glycemic range to a target glycemic range corresponding to a healthy glycemic state.

16 Claims, 15 Drawing Sheets

(56) References Cited

U.S. PATENT DOCUMENTS

| | | | |
|---|---|---|---|
| 2014/0350369 A1* | 11/2014 | Budiman | A61B 5/4848 600/365 |
| 2015/0148774 A1* | 5/2015 | Yao | A61M 5/1723 604/504 |
| 2015/0190100 A1* | 7/2015 | Fox | G16H 40/63 340/539.12 |
| 2015/0289821 A1* | 10/2015 | Rack-Gomer | G16H 40/63 600/365 |
| 2016/0039496 A1* | 2/2016 | Hancock | G01S 19/19 701/60 |

* cited by examiner

500

501
Acquire physiological data specifying blood glucose level over a first time interval

502
Calculate a TIR measure for a first glycemic range over the first time interval

503
Determine whether the TIR measure exceeds a specified threshold

504
Receive input indicative of user input provided at a software program

505
Identify a second glycemic range

506
Cause a notification specifying the second glycemic range to be presented

601
Acquire physiological data specifying blood glucose level over a first time interval

602
Calculate a first TIR measure for a first glycemic range over the first time interval

603
Identify a second glycemic range

604
Acquire physiological data specifying blood glucose level over a second time interval

605
Calculate a second TIR measure for the second glycemic range over the second time interval

606
Identify a third glycemic range

607
Cause a graphical representation to be created that visually depicts directionality of blood glucose level over time

701
Identify at least one previous glycemic range

702
Examine total range covered by the at least one previous glycemic range

703
Set bounds of a subsequent glycemic range

704
Predict whether the subsequent glycemic range is within an appropriate range

TIERED TIME-IN-RANGE GUIDING INTERFACES FOR DIABETES MANAGEMENT

TECHNICAL FIELD

Various embodiments concern software programs and associated interfaces for guiding people with diabetes toward a target glycemic range corresponding to a healthy glycemic state.

BACKGROUND

After ingestion of a foodstuff that contains carbohydrates, the human body breaks down the carbohydrates into glucose, which serves as a source of energy for the cells of the human body. Glucose is transported via circulation within the blood stream. Therefore, ingestion of foodstuffs will influence the concentration of glucose within the blood stream (also referred to as the "blood glucose level" or "glucose level").

According to the American Diabetes Association (ADA), a normal blood glucose level for people without diabetes is below 6.9 mmol/L (125 mg/dL). Meanwhile, the target blood glucose range for people with diabetes is 5.0-7.2 mmol/L (90-130 mg/dL) before meals and less than 10 mmol/L (180 mg/dL) after meals. However, some people with diabetes struggle to consistently stay within the recommended range.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references may indicate similar elements.

FIG. 5 depicts a flow diagram of a process for producing personalized glycemic goals based on physiological data that is examined by a diabetes management platform.

FIG. 6 depicts a flow diagram of a process for managing diabetes through the production of glycemic ranges that guide an individual toward a target glycemic range.

FIG. 7 depicts a flow diagram of a process for identifying a subsequent glycemic range based on one or more previous glycemic ranges.

Figure 1:
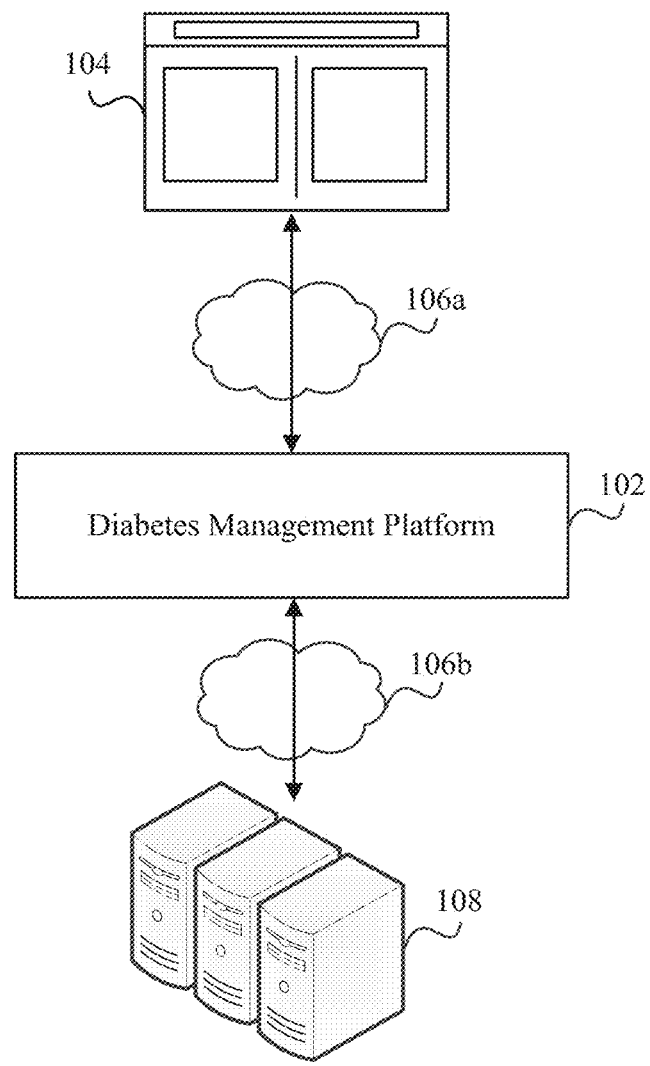
FIG. 1 illustrates a network environment that includes a diabetes management platform.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Diabetes mellitus (commonly referred to as "diabetes") is a group of metabolic disorders in which the affected individuals experience high blood glucose levels over a prolonged period. If left untreated, diabetes can cause many complications. For example, long-term complications can include cardiovascular disease, stroke, chronic kidney disease, foot ulcers, and eye damage.

Individuals with diabetes can benefit from education about treatment, good nutrition to achieve a normal body weight, and exercise. However, those individuals often find it difficult to implement lifestyle changes that promote healthier blood glucose levels. Moreover, those individuals often find it difficult to understand blood glucose level measurements, which represent a technical signal indicative of the diabetes disease state.

Introduced here, therefore, are diabetes management platforms able to guide people with diabetes toward a target. More specifically, a diabetes management platform can develop glycemic goals intended to guide an individual with diabetes along a personalized route toward a target. The target may be a glycemic range considered to be normal by the American Diabetes Association (ADA). Thus, the target may be a glycemic range corresponding to a healthy glycemic state.

Rather than state the absolute amount of glucose within the blood, a diabetes management platform can instead be configured to produce personalized glycemic goals based on physiological data associated with a specified individual.

The diabetes management platform may also be configured to show the directionality of blood glucose level over time (e.g., whether blood glucose level is trending toward or away from the target).

These glycemic goals can be based on several different measures indicative of a healthy glycemic state. For example, an ambulatory glucose profile (AGP) offers a standard visualization of blood glucose level that is readily understandable. Similar to an electrocardiogram in cardiology, the AGP can collapse physiological data collected over several days or weeks into a single 24-hour period, thereby creating a model day. The AGP can reveal underlying patterns in blood glucose variability to a greater extent than static measurements. The AGP incorporates several key metrics in guiding diabetes treatment, including: time in range (TIR), time above range (TAR), time below range (TBR), glycemic variability (GV), glycemic exposure, and ranges for hypoglycemia and hyperglycemia.

Because TIR is an intuitive parameter that is readily understood by most individuals with diabetes, the diabetes management platform may use TIR to produce personalized sets of glycemic goals. More specifically, the diabetes management platform can acquire physiological data associated with an individual, calculate TIR for a specified glycemic range, and then formulate a glycemic goal. The glycemic goal may be based on the TIR and/or the specified glycemic range.

For example, if the diabetes management platform determines that the time spent within a first glycemic range exceeds a specified threshold, then the diabetes management platform may recommend that the individual attempt to keep their blood glucose level within a second glycemic range. Generally, the second glycemic range is closer than the first glycemic range to a target glycemic range corresponding to a healthy glycemic state.

Embodiments may be described with reference to particular computer programs, system configurations, networks, etc. However, those skilled in the art will recognize that the features described herein are equally applicable to other computer program types, system configurations, network types, etc. Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device to perform a process for developing personalized glycemic goals intended to guide an individual toward a healthier glycemic range, generating interfaces that specify progress toward the personalized glycemic goals, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, two devices may be electrically or communicatively coupled to one another despite not sharing a physical connection.

The term "module" refers broadly to software components, hardware components, and/or firmware components. Modules are typically functional components that can generate useful data or other output(s) based on specified input(s). A module may be self-contained. A software program may include one or more modules.

When used in reference to a list of multiple items, the word "or" is intended to cover all of the following interpretations: any of the items in the list, all of the items in the list, and any combination of items in the list.

Technology Overview

FIG. 1 illustrates a network environment 100 that includes a diabetes management platform 102. Individuals can interface with the diabetes management platform 102 via an interface 104. The diabetes management platform 102 may be responsible for parsing physiological data pertaining to an individual to determine certain measure(s) that may be useful in guiding the individual toward a healthier state. The diabetes management platform 102 may also be responsible for creating interfaces through which the individual can view physiological data, manage preferences, etc.

Physiological data could specify the blood glucose level of the individual accessing the interface 104 or some other person. For example, in some embodiments the interface 104 enables a person with diabetes to view their own physiological data, while in other embodiments the interface 104 enables an individual to view physiological data associated with another person. The individual may be a medical professional (e.g., a physician or nurse), a family member of the person with diabetes, etc.

As noted above, the diabetes management platform 102 may reside in a network environment 100. Thus, the diabetes management platform 102 may be connected to one or more networks 106a-b. The network(s) 106a-b can include local area networks (LANs), wide area networks (WANs), metropolitan area networks (MANs), cellular networks, the Internet, etc. The diabetes management platform 102 may also communicate with other computing devices over a short-range communication protocol, such as Bluetooth® or Near Field Communication (NFC).

The interface 104 is preferably accessible via some combination of a web browser, desktop software program, mobile application, or over-the-top (OTT) application. Accordingly, the interface 104 may be viewed on a personal computer, tablet computer, personal digital assistant (PDAs), mobile phone, game console (e.g., Sony PlayStation® or Microsoft Xbox®), music player (e.g., Apple iPod Touch®), wearable electronic device (e.g., a watch or fitness band), network-connected ("smart") device (e.g., a television or home assistant device), virtual/augmented reality system (e.g., a head-mounted display such as Oculus Rift® and Microsoft Hololens®), or some other electronic device.

Some embodiments of the diabetes management platform 102 are hosted locally. That is, the diabetes management platform 102 may reside on the computing device used to access the interface 104. For example, the diabetes management platform 102 may be embodied as a mobile application executing on a mobile phone. Other embodiments of the diabetes management platform 102 are executed by a cloud computing service operated by Amazon Web Services® (AWS), Google Cloud Platform™, Microsoft Azure®, or a similar technology. In such embodiments, the diabetes management platform 102 may reside on a host computer server that is communicatively coupled to one or more content computer servers 108. The content computer server(s) 108 can include different types of data, user information (e.g., profiles, credentials, and health-related information), and other assets. Additionally or alternatively, such information could be stored on the host computer server.

Certain embodiments are described in the context of network-accessible interfaces. However, those skilled in the art will recognize that the interfaces need not necessarily be accessible via a network. For example, a computing device may be configured to execute a self-contained software program that does not require network access. Instead, the self-contained software program may cause necessary assets (e.g., physiological data, healthcare regimen data, and processing operations) to be downloaded at a single point in time or on a periodic basis (e.g., weekly, hourly, or daily).

Figure 2:
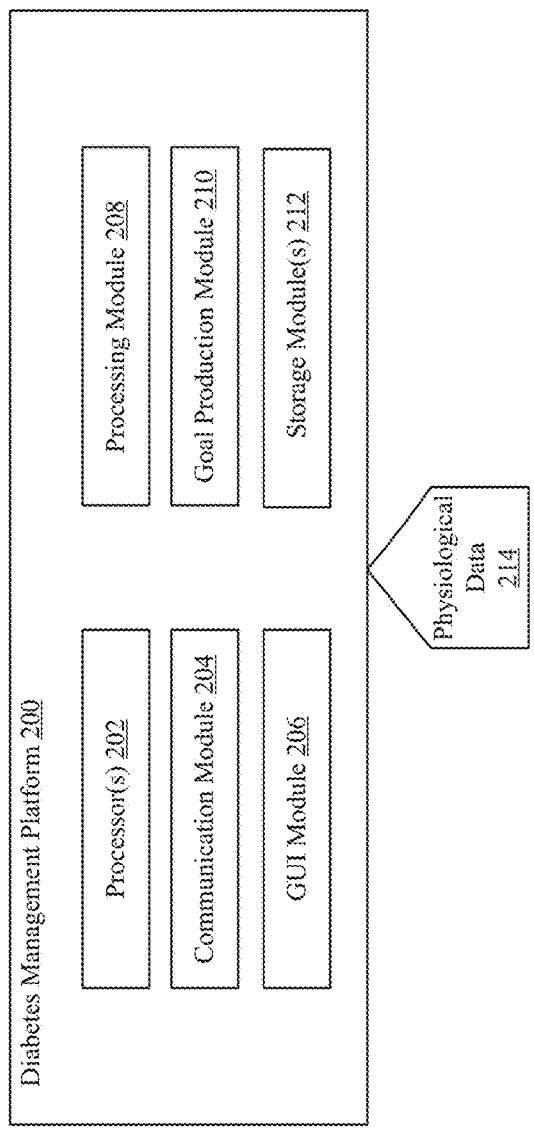
FIG. 2 depicts the high-level architecture of a diabetes management platform able to produce personalized glycemic goals that are intended to guide an individual toward a healthy glycemic state.

FIG. 2 depicts the high-level architecture of a diabetes management platform 200 able to produce personalized glycemic goals that are intended to guide an individual toward a healthy glycemic state. As shown in FIG. 1, an individual can interface with the diabetes management platform 200 via an interface. The individual may be a person with diabetes or another person with an interest in the blood glucose levels of the person with diabetes.

The diabetes management platform 200 can include one or more processors 202, a communication module 204, a graphical user interface (GUI) module 206, a processing module 208, a goal production module 210, and one or more storage modules 212. In some embodiments a single storage module includes multiple computer programs for performing different operations (e.g., format conversion, temporal alignment, statistical analysis), while in other embodiments each computer program is hosted within a separate storage module. Embodiments of the diabetes management platform 200 may include some or all of these components, as well as other components not shown here.

The processor(s) 202 can execute modules (e.g., the processing module 208 and the goal production module 210) from instructions stored in the storage module(s) 212, which can be any device or mechanism capable of storing information. The communication module 204 can manage communications between various components of the diabetes management platform 200. The communication module 204 can also manage communications between the computing device on which the diabetes management platform 200 resides and another computing device.

For example, the diabetes management platform 200 may reside on a mobile phone in the form of a mobile application. In such embodiments, the communication module 204 can facilitate communication with a network-accessible computer server responsible for supporting the mobile application. The communication module 204 may facilitate communication with various data sources through the use of application programming interfaces (APIs), bulk data interfaces, etc.

As another example, the diabetes management platform 200 may reside on a server system that includes one or more network-accessible computer servers. In such embodiments, the communication module 204 can communicate with a software program executing on the computing device associated with the individual. Those skilled in the art will recognize that the components of the diabetes management platform 200 can be distributed between the server system and the computing device associated with the individual in various manners. For example, some data (e.g., physiological data) may reside on the computing device of the individual, while other data (e.g., processing operations, previous glycemic ranges and TIR measures, indicators of progress toward a target glycemic range) may reside on the server system.

The GUI module 206 can generate the interface(s) through which an individual can interact with the diabetes management platform 200. For example, an interface may include a graphical representation of blood glucose level over time. As another example, an interface may include depicts graphical representation of glycemic ranges over time, thereby showing the directionality of the blood glucose level (e.g., whether the individual is trending toward or away from a target glycemic range). These interfaces may also present suggestions for improving the health state (e.g., by performing certain activities, refraining from consuming certain foodstuffs, etc.).

The processing module 208 can apply one or more operations to physiological data 214 acquired by the diabetes management platform 200. Physiological data 214 specifying the blood glucose level of an individual could be generated by a glucose monitoring device. Examples of glucose monitoring devices include continuous glucose monitors (e.g., Medtronic Enlite® Sensor) and blood glucose meters (e.g., Bayer Contour®).

A glucose monitoring device may be configured to continuously or periodically transmit physiological data 214 to the diabetes management platform. In some embodiments, the glucose monitoring device continually uploads physiological data 214 to the diabetes management platform 200 so long as the glucose monitoring device remains communicatively coupled to the computing device on which the diabetes management platform 200 resides (e.g., via a Bluetooth® channel). In other embodiments, the glucose monitoring device periodically uploads physiological data 214 to the diabetes management platform 200 on a periodic basis (e.g., hourly, daily, weekly). In such embodiments, the physiological data 214 may include multiple data sets (e.g., a first data set for a first time interval, a second data set for a second time interval, etc.).

The processing module 208 can parse the physiological data 214 to identify certain characteristic(s) of the blood glucose level. For example, the processing module 208 may calculate metrics that are critical in guiding diabetes treatment in a personalized manner. These metrics can include TIR, GV, glycemic exposure, and ranges for hypoglycemia and hyperglycemia.

The goal production module 210 may use these metrics to produce personalized glycemic goals for an individual. More specifically, the goal production module 210 may identify a glycemic range within which the individual is expected to remain based on a TIR measure associated with a prior glycemic range. For example, if the processing module 208 determines that the individual maintained a blood glucose level of 7.2-8.3 mmol/L (130-150 mg/dL) more than 83% percent of the time over the course of a week, then the goal production module 210 may recommend that the individual attempt to maintain a blood glucose level of 6.7-7.8 mmol/L (120-140 mg/dL) over the following week. Those skill in the art will recognize that personalized glycemic goals could be created for various time intervals (e.g., a day, week, or month). As further described below, by periodically identifying glycemic ranges that represent quantitative glycemic goals, the diabetes management platform 200 can guide the individual toward a target glycemic range corresponding to a healthy glycemic state.

Figure 3:
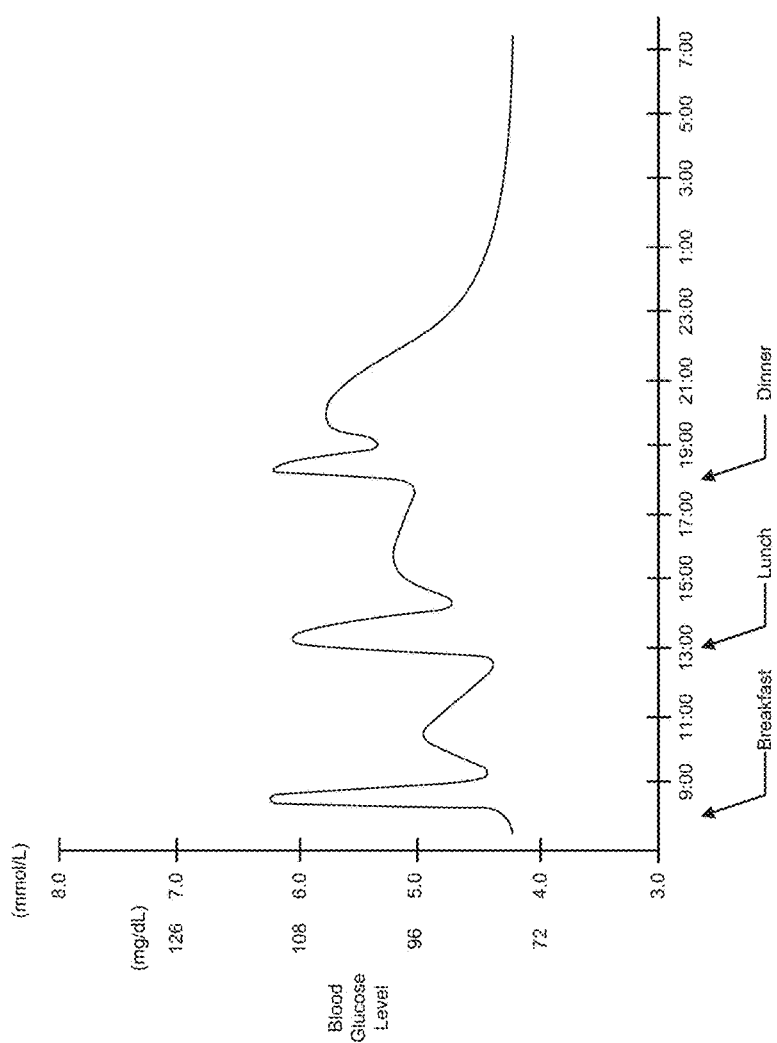
FIG. 3 illustrates how blood glucose levels can vary throughout the day.

FIG. 3 illustrates how blood glucose levels can vary throughout the day. As shown here, the blood glucose level will increase following the ingestion of food, and then steadily decrease thereafter. Foods having a high glycemic index are more rapidly digested, and thus cause substantial fluctuations in the blood glucose level over a short period of time.

According to the ADA, a normal blood glucose level for people without diabetes is below 6.9 mmol/L (125 mg/dL). Meanwhile, the target blood glucose range for people with diabetes is 5.0-7.2 mmol/L (90-130 mg/dL) before meals and less than 10 mmol/L (180 mg/dL) after meals. However, some people with diabetes struggle to consistently stay within the recommended range. For example, individuals with blood glucose levels that are consistently above 7.0 mmol/L (126 mg/dL) are generally considered to have hyperglycemia, while individuals with blood glucose levels that are consistently below 4.0 mmol/L (70 mg/dL) are generally considered to have hypoglycemia.

The ambulatory glucose profile (AGP) is a methodology for interpreting the daily glucose patterns of an individual. The AGP can provide both graphical characterizations and quantitative characterizations of diurnal blood glucose patterns, thereby making it possible to identify previously-undetectable abnormalities in glucose metabolism. The AGP can be used for representation of self-monitored blood glucose (SMBG) data and continuation glucose monitoring (CGM) data.

Figure 4:
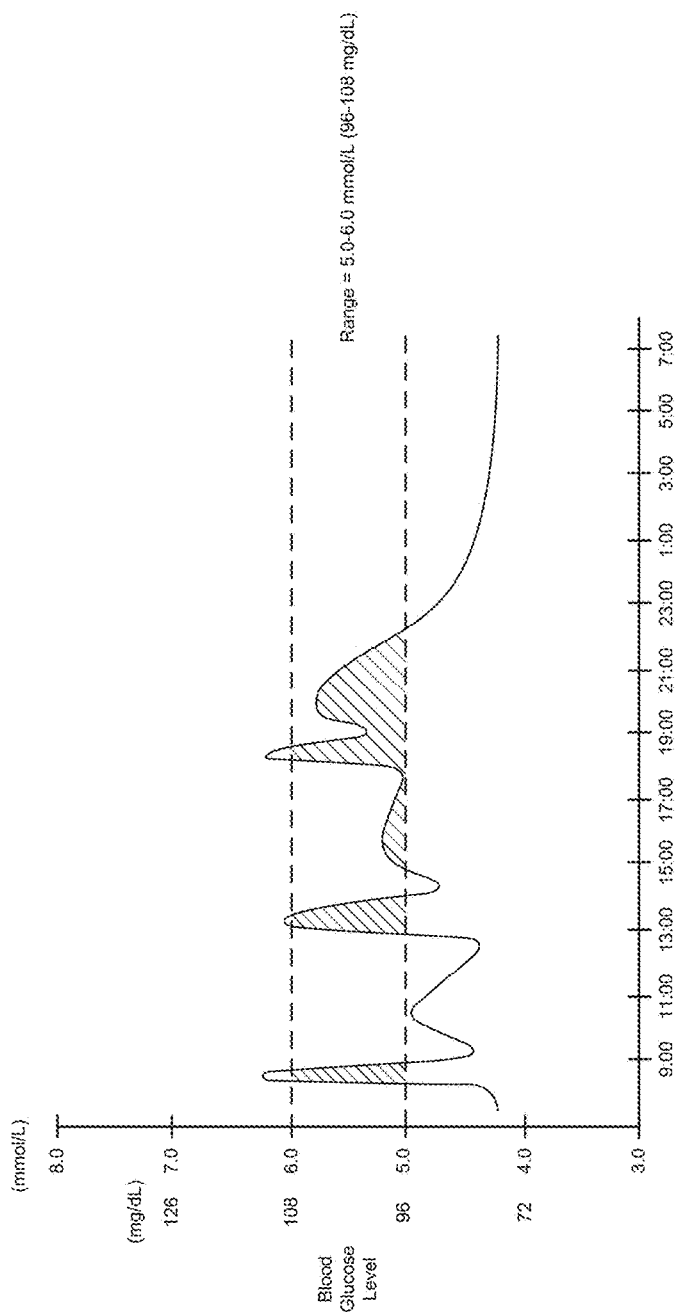
FIG. 4 illustrates how time in range (TIR) quantifies the time spent within a specified glycemic zone over the course of a specified time interval.

One key metric incorporated into the AGP is TIR. As shown in FIG. 4, TIR is an intuitive parameter that quantifies the time spent within a specified glycemic zone over the course of a specified time interval. Here, for example, the shaded area represents TIR for 5.0-6.0 mmol/L (96-108 mg/dL) over the course of a single day. While the blood glucose level is likely to reside outside of the specified glycemic zone for at least part of the day, TIR provides a qualitative metric that is generally indicative of the glycemic health of an individual.

FIG. 5 depicts a flow diagram of a process 500 for producing personalized glycemic goals based on physiological data that is examined by a diabetes management platform (e.g., diabetes management platform 200 of FIG. 2). Initially, the diabetes management platform acquires physiological data specifying the blood glucose level of an individual over a first time interval (step 501). The physiological data may be generated by a glucose monitoring device that monitors the blood glucose level of the individual. For example, the glucose monitoring device may be a continuous glucose monitor that continuously monitors the blood glucose level or a blood glucose meter that periodically monitors the blood glucose level. The first time interval could be a day, week, month, or some other specified time period (e.g., 6 hours or 12 hours).

The diabetes management platform can then calculate a TIR measure indicative of the duration during which the blood glucose level was within a first glycemic range during the first time interval (step 502). This can be accomplished in several ways. For example, if the glucose monitoring device is a continuous glucose monitor, then the diabetes management platform can integrate the substantially-continuous waveform that can be produced using the CGM data. However, if the glucose monitoring device is a blood glucose meter, then the diabetes management platform may perform retrospective pattern analysis on SMBG data (e.g., considering the AGP associated with the individual).

The diabetes management platform can then determine whether the TIR measure exceeds a specified threshold (step 503). The specified TIR measure may be a predetermined percentage of the first time interval (e.g., 50%, 75%, or 83%).

In some embodiments, the diabetes management platform also receives input indicative of user input provided at a software program associated with the diabetes management platform (step 504). The input may specify whether a glycemic range modification is desired by the individual. For example, if the individual knows that an upcoming event (e.g., a vacation or party) is likely to increase the average blood glucose value for an upcoming time interval, then the individual may request that the diabetes management platform refrain from modifying the bounds of the glycemic range in which the individual is expected to remain during the upcoming time interval. The software program may be a web browser, desktop software program, mobile application, or OTT application.

The diabetes management platform can then identify a second glycemic range within which the blood glucose level of the individual is expected to remain during a second time interval (step 505). The second time interval may be the same as, or different than, the first time interval. Thus, the second time interval could be a day, week, month, or some other specified time period (e.g., 6 hours or 12 hours).

The second glycemic range may be based on the first glycemic range, the TIR measure, and/or the input. For example, in response to a determination that the TIR measure exceeds the specified threshold, the diabetes management platform may identify a second glycemic range that is lower than the first glycemic range. As another example, in response to a determination that the TIR measure does not exceed the specified threshold, the diabetes management platform may identify a second glycemic range that is substantially identical to the first glycemic range.

In some embodiments, the second glycemic range is also based on the diabetes management success of a cohort that includes the individual. For example, the diabetes management platform may identify an appropriate glycemic range based on the glycemic ranges typically recommended to other cohort members. More specifically, the diabetes management platform may increase/decrease the rate at which the glycemic ranges provided to the individual approach a target glycemic range based on the success of other cohort members (e.g., by observing whether other cohort members tend to plateau at a certain point). The cohort can include members sharing a characteristic in common, such as race, age, sex, medication regimen, diabetes type, etc.

For example, if the diabetes management platform determines that the individual maintained a blood glucose level of 7.2-8.3 mmol/L (130-150 mg/dL) more than 83% percent of the time over the course of a week, then the diabetes management platform may recommend that the individual attempt to maintain a blood glucose level of 6.7-7.8 mmol/L (120-140 mg/dL) over the following week. Thus, the first glycemic range and the second glycemic range may partially overlap. Generally, the second glycemic range is closer than the first glycemic range to a target glycemic range corresponding to a healthy glycemic state. Consequently, the diabetes management platform may guide the individual toward the target glycemic range over time based on whether the individual is successful in achieving personalized glycemic goals associated with certain glycemic ranges.

However, the second glycemic range could also be substantially identical to the first glycemic range. For example, if the diabetes management platform determines that the individual maintained a blood glucose level of 7.2-8.3 mmol/L (130-150 mg/dL) less than 83% percent of the time over the course of a week, then the diabetes management platform may recommend that the individual attempt to maintain the same blood glucose level of 7.2-8.3 mmol/L (130-150 mg/dL) over the following week. Thus, the first glycemic range and the second glycemic range may entirely overlap.

Moreover, the diabetes management platform may be configured to dynamically adjust glycemic ranges and multi-tiered glycemic thresholds based on the blood glucose level history of the individual, contextual information derived from an event involving the individual, or some combination thereof. For example, the diabetes management platform may dynamically adjust a glycemic range based on an adjustable parameter that is manually specified by the individual (e.g., a patient), manually specified by another individual (e.g., a medical professional, family member, or coach), or dynamically generated by the diabetes management platform and confirmed by the individual and/or the other individual, Contextual information, meanwhile, may be derived from an electronic device associated with the individual, such as a fitness tracker, mobile phone, etc.

The diabetes management platform can also cause a notification specifying the second glycemic range to be presented by a computing device associated with the individual (step 506). The notification could be a visual notification, an audible notification, a tactile notification, or any combination thereof. For example, if the diabetes management platform resides on a mobile phone in the form of a mobile application, then the notification may be a push notification created by the mobile application. As another example, the notification may be delivered by a chat bot accessible via the mobile application. Those skilled in the art will recognize that notifications could also be delivered as e-mail messages, Short Message Service (SMS) messages (commonly referred to as "text messages"), etc.

FIG. 6 depicts a flow diagram of a process 600 for managing diabetes through the production of glycemic ranges that guide an individual toward a target glycemic range. These glycemic ranges are intended to guide the individual toward the target glycemic range over time based on whether the individual is successful in achieving personalized glycemic goals. Because the personalized glycemic goals are readily achievable, the individual is more likely to successfully achieve the personalized glycemic goals (and thus approach the target glycemic range). Steps 601-603 of FIG. 6 are substantially similar to steps 501-502 and 505 of FIG. 5.

However, after identifying the second glycemic range, the diabetes management platform may acquire physiological data specifying the blood glucose level of the individual over the second time interval (step 604). The physiological data pertaining to the second time interval will typically be generated by the same glucose monitoring device that generated the physiological data pertaining to the first time interval. Physiological data may be acquired in the form of multiple data sets (e.g., a first data set for the first time interval and a second data set for a second time interval).

The diabetes management platform can calculate a TIR measure indicative of the duration during which the blood glucose level was within the second glycemic range during the second time interval (step 605). The diabetes management platform can then identify a third glycemic range within which the blood glucose level of the individual is expected to remain during a third time interval (step 606). The third time interval may be the same as, or different than, the first time interval and the second time interval. For example, the first time interval, the second time interval, and the third time interval may represent consecutive days, weeks, or months.

The third glycemic range may be based on the first glycemic range, the TIR measure corresponding to the first glycemic range, the second glycemic range, the TIR measure corresponding to the second glycemic range, etc. The diabetes management platform may consider characteristic(s) of multiple previous glycemic ranges when identifying a new glycemic range for the individual. For example, the diabetes management platform may ensure that the lower bound of the glycemic range does not decrease by more than a specified amount (e.g., 1.0 mmol/L or 18 mg/dL) over a specified time period (e.g., two weeks or four weeks).

Execution of the process 600 enables the diabetes management platform to guide the individual toward a target glycemic range in a personalized manner. The target glycemic range could be, for example, the glycemic range corresponding to a healthy glycemic state as defined by the ADA. Accordingly, the second glycemic range will typically be closer to the target glycemic range than the first glycemic range, and the third glycemic range will typically be closer to the target glycemic range than the second glycemic range. However, as noted above, there may be some instances in which the same glycemic range is recommended by the diabetes management platform over consecutive time intervals.

As further described below, the diabetes management platform may also cause a graphical representation to be created that visually depicts the directionality of the blood glucose level over time (step 607). The graphical representation may be provided to the individual in one or more formats. For example, the graphical representation may be made accessible to the individual via a mobile application, web browser, etc. As another example, the graphical representation may be embedded within an e-mail that is delivered to an e-mail address associated with the individual on a periodic basis (e.g., monthly, weekly, or daily).

Here, the process 600 manages diabetes through the production of glycemic ranges that guide an individual toward a target glycemic range. However, a similar process may be performed by the diabetes management platform in which different TIR measures for a single glycemic range are recommended over time.

For example, the diabetes management platform may initially recommend that the individual attempt to achieve a first TIR measure (e.g., 50%) with respect to a glycemic range (e.g., 5.0 mmol/L (90 mg/dL)-10 mmol/L (180 mg/dL)) over a first time interval. Responsive to a determination that the individual was able to achieve the first TIR measure over the first time interval, the diabetes management platform may recommend that the individual attempt to achieve a second TIR measure (e.g., 60%) with respect to the same glycemic range over a second time interval. Although the glycemic range remains the same over consecutive time intervals in such embodiments, the increasing TIR measures can still promote a healthier glycemic state.

FIG. 7 depicts a flow diagram of a process 700 for identifying a subsequent glycemic range based on one or more previous glycemic ranges. Thus, the steps of process 700 may be performed during step 505 of FIG. 5 or step 603 of FIG. 6.

Initially, the diabetes management platform can identify at least one previous glycemic range associated with an individual (step 701). For example, if the individual has recently begun a diabetes management program, then a single previous glycemic range may be associated with the individual. However, if the individual has been assigned to a diabetes management program for a longer time period (e.g., weeks or months), then multiple previous glycemic ranges may be associated with the individual.

The diabetes management platform can examine the total range covered by the at least one previous glycemic range (step 702). The total range is indicative of progress the individual has made over time toward a target glycemic range.

The diabetes management platform can then set the bounds of a subsequent glycemic range (step 703). The upper and lower bounds of the subsequent glycemic range can be based on one or more factors, including:

- The bounds of the previous glycemic range(s). For example, the diabetes management platform may set the subsequent glycemic range a predetermined distance away from the immediately preceding glycemic range (e.g., the upper and lower bounds may be reduced by a specified amount, such as 0.55 mmol/L (10 mg/dL) or 1.1 mmol/L (20 mg/dL)).
- The success in maintaining a blood glucose level within the previous glycemic range(s). For example, if the diabetes management platform determines that the individual was able to accomplish a personalized glycemic goal that required a 5% lowering of the glycemic range, then the diabetes management platform may recommend another 5% lowering of the glycemic range. Similarly, if the diabetes management platform determines that the individual was not able to accomplish a personalized glycemic goal that required a 10% lowering of the glycemic range, then the diabetes management platform may recommend a smaller lowering of the glycemic range.
- Statistical models summarizing the progression of the individual over time, the likelihood that the individual will achieve a proposed glycemic goal, etc.
- Comparisons of glycemic range progression with a cohort that includes the individual.

Moreover, in some embodiments, the diabetes management platform predicts whether the subsequent glycemic range is within an appropriate range (step 704). Thus, the diabetes management platform may determine whether the individual is likely to spend a certain duration of time within the subsequent glycemic range (i.e., achieve the personalized glycemic goal proposed by the diabetes management platform). Such action may be based on the past success of the individual in achieving personalized glycemic goals, the success of other individuals in the cohort in achieving similar glycemic goals, the difference between consecutive glycemic ranges (e.g., success is generally more likely as the difference decreases), etc.

Thus, the diabetes management platform can dynamically recommend appropriate glycemic ranges based on previously-collected physiological data associated with the individual. Said another way, recommendations produced by the diabetes management platform are rarely static in nature, though they may be at least partially based on static measurements included in a diabetes management program.

Unless contrary to physical possibility, it is envisioned that the steps described above may be performed in various sequences and combinations. For example, the diabetes management platform may periodically execute these processes such that glycemic ranges are recommended on a periodic basis (e.g., monthly, weekly, or daily). Such a feature enables the diabetes management platform to guide an individual toward a healthier glycemic status over the course of weeks, months, years, etc.

Other steps may also be included in some embodiments. For example, the diabetes management platform can configure a patient profile corresponding to a specified individual with multi-tiered glycemic thresholds. Each lower tier may correspond to a narrower target glycemic range as compared to a wider target glycemic range corresponding to an upper tier. Presentation of these multi-tiered glycemic thresholds to the specified individual may guide the specified individual toward the narrower target glycemic range in a manner susceptible to behavior change. Said another way, guiding the specified individual toward a healthy glycemic range over time is more likely to result in lasting behavior changes than an abrupt demand (which is more likely to be difficult or impossible for the specified individual to achieve). The patient profile may be associated with an electronic device and a glucose monitoring device.

In some embodiments, configuring the patient profile includes dynamically adjusting, based on blood glucose level history of the specified individual, data from an electronic device that is indicative of a contextual event involving the specified individual, the multi-tiered glycemic thresholds, or a combination thereof. In other embodiments, configuring the patient profile includes dynamically adjusting, based on blood glucose level history of the specified individual, data from an electronic device that is indicative of a contextual event involving the individual, a time interval during which blood glucose levels are monitored, a subsequent time interval during which blood glucose levels are monitored, or a combination thereof. Moreover, these dynamic adjustments can be performed based on an adjustable parameter that is manually specified by the individual, manually specified by another individual, or dynamically generated by the processor and confirmed by the individual or the other individual.

Figure 8A:
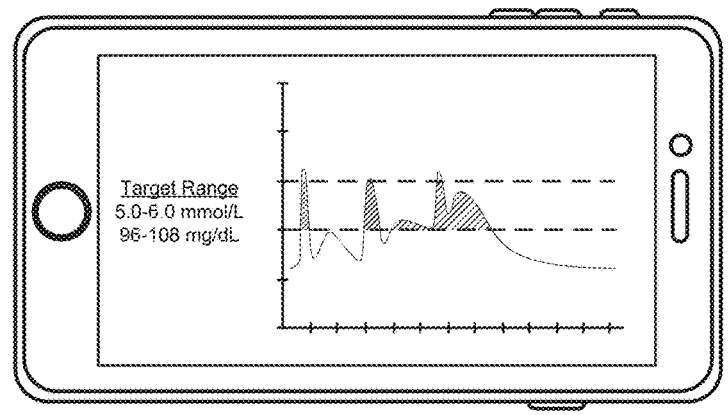
FIG. 8A depicts an interface that shows blood glucose level over time for an individual.
Figure 8B:
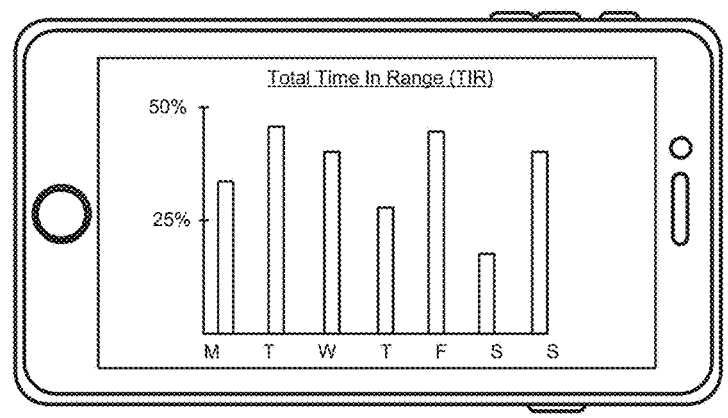
FIG. 8B depicts an interface that shows TIR for sub-intervals of a time interval (here, days in a weeklong time interval).
Figure 8C:
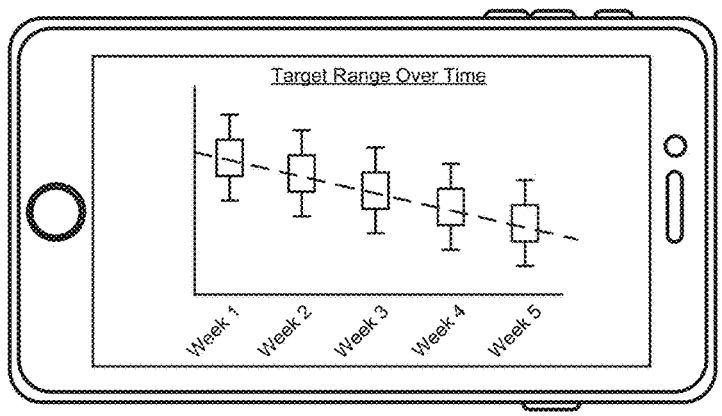
FIG. 8C depicts an interface that shows the glycemic ranges recommended for an individual over time, as well as a trend line showing the directionality of blood glucose level over time.

FIGS. 8A-C depict several examples of interfaces that may be produced by a diabetes management platform. While these interfaces are illustrated as mobile application interfaces accessible via a mobile phone, those skilled in the art will recognize that similar interfaces may be accessible via a web browser, desktop software program, OTT application, etc.

FIG. 8A depicts an interface that shows blood glucose level over time for an individual. The interface may enable the individual to manually specify a particular timeframe over which blood glucose level will be shown. For example, the interface may show blood glucose level over the course of a day, week, month, etc. In some embodiments the interface simply plots blood glucose level versus time, while in other embodiments the shades in certain areas that may be of interest to the individual. Here, for example, the areas corresponding to a TIR measure are shaded.

Similarly, the interface may plot blood glucose level over time by ignoring the date and subjecting the corresponding data to smoothing (e.g., using multiple frequency percentile curves). That is, the interface may present the AGP for the individual. Upon observing the AGP, the individual may notice areas of significant variability that are indicative of the diabetes disease state.

FIG. 8B depicts an interface that shows TIR for subintervals of a time interval (here, days in a weeklong time interval). The interface may enable the individual to provide comment(s) with respect to certain days. For example, the individual may specify that they attended an event on Saturday that prohibited them from achieving a higher TIR measure. Such input may permit the diabetes management platform to lessen the impact certain time intervals have on any recommendations provided. For example, the diabetes management platform may lessen the impact of one-time events, or disregard the time intervals corresponding to these one-time events completely.

FIG. 8C depicts an interface that shows the glycemic ranges recommended for an individual over time, as well as a trend line showing the directionality of blood glucose level over time. As noted above, a diabetes management platform may guide the individual toward a target glycemic range by recommending a glycemic range within which the blood glucose level is expected to remain during an upcoming time interval. By plotting these recommended glycemic ranges over time, the interface can illustrate progress toward the target glycemic range.

Use Cases

Interfaces produced by the diabetes management platform introduced here enables individuals to readily monitor their own blood glucose levels. More specifically, consistent use of these interfaces over time allows the individuals to better control their diabetes, as well as improve their overall state of health.

In one example, an individual (John Doe) has diabetes. Before using the diabetes management platform, John Doe consistently struggles with controlling his blood glucose levels. The blood glucose range of John Doe typically exceeds 8.0 mmol/L (145 mg/dL) before meals and 11.0 mmol/L (196 mg/dL) after meals. However, the ADA specifies that the target blood glucose range for people with diabetes is 5.0-7.2 mmol/L (90-130 mg/dL) before meals and less than 10 mmol/L (180 mg/dL) after meals. The diabetes management platform (and associated interfaces) can present this information in a manner that is easily understood by John Doe. John Doe is more likely to incorporate healthy habits into his lifestyle because he can see progress that has been made.

For example, as John Doe consumes meals throughout the week, his blood glucose level will rise and fall. A glucose monitoring device (e.g., a continuous glucose monitor or blood glucose meter) can detect the blood glucose level as measurements are made. Physiological data indicative of the blood glucose level can be transmitted to the diabetes management platform.

The diabetes management platform can parse physiological data to identify an initial glycemic range (e.g., a first glycemic range). The initial glycemic range can be identified in several different ways. For example, the diabetes management platform may set the average pre-meal blood glucose level as the lower bound and the average post-meal blood glucose level as the upper bound. As another example, the diabetes management platform may identify the blood glucose range having the highest TIR measure. For instance, the diabetes management platform may calculate TIR measures for 8.3-9.4 mmol/L (150-170 mg/dL), 8.9-10.0 mmol/L (160-180 mg/dL), 9.4-10.5 mmol/L (170-190 mg/dL), etc. These ranges have been selected for the purpose of illustration. Those skilled in the art will recognize that other ranges could also be used.

Thereafter, John Doe can continue consuming meals as he normally would. The diabetes management platform can examine the physiological data following the conclusion of a specified time interval. For example, the diabetes management platform may calculate a TIR measure indicative of the duration during which John Doe's blood glucose level was within the initial glycemic range over the course of a week.

The diabetes management platform can then identify a subsequent glycemic range (e.g., a second glycemic range). For example, if the TIR measure exceeds a specified threshold, then the bounds of the subsequent glycemic range may be lower than the bounds of the initial glycemic range. As another example, if the TIR measure does not exceed the specified threshold, then the bounds of the subsequent glycemic range may be substantially similar to the bounds of the initial glycemic range.

Generally, a subsequent glycemic range will be based on at least one prior glycemic range. For example, the diabetes management platform may set the subsequent glycemic range a predetermined distance away from a previous glycemic range (e.g., so long as the TIR measure exceeds the specified threshold, the upper and lower bounds may be reduced by a specified amount, such as 0.55 mmol/L (10 mg/dL) or 1.1 mmol/L (20 mg/dL)). As another example, the diabetes management platform may predict (e.g., by using statistical models based on John Doe's previous glycemic ranges or by comparing John Doe's glycemic range progression with a cohort) whether the subsequent glycemic range will be within an acceptable range.

Such action allows the diabetes management platform to produce personalized glycemic goals that are intended to guide John Doe toward a healthier glycemic state. Moreover, because the personalized glycemic goals are readily achievable, John Doe is more likely to successfully achieve the personalized glycemic goals. For example, John Doe may only need to make minor lifestyle adjustments to meet a 2.5%, 5%, or 10% change in the glycemic range over consecutive weeks.

Because the diabetes management platform can examine all physiological data generated by a glucose monitoring device, the diabetes management platform can also create personalized recommendations for John Doe. For example, the diabetes management platform may discover that certain meals (e.g., lunch or dinner), foods (e.g., pasta or bagels), and/or locations (e.g., a specified restaurant) cause John Doe to exceed his recommended glycemic range. The diabetes management platform may recommend that John Doe limit consumption based on these discoveries. For example, the diabetes management platform may produce a notification during the early evening that warns John Doe against overeating at dinner. As another example, the diabetes management platform may produce a notification that recommends John Doe refrain from consuming a specified foodstuff at a specified restaurant known to cause a significant increase in blood glucose level.

In another example, an individual (Jane Doe) is presented with a series of interfaces intended to guide Jane Doe toward a healthier glycemic state. As further described below, these interfaces may enable Jane Doe to set time-in-zone (TIZ) targets, provide periodic recommendations, generate periodic reports on glycemic goal process, etc.

Figure 9B:
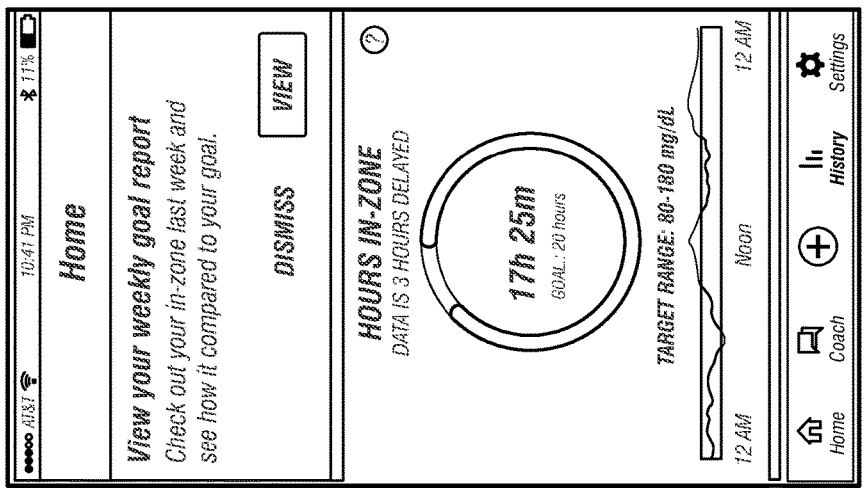
FIG. 9B depicts an example of a notification window that overlays the dashboard interface.
Figure 9A:
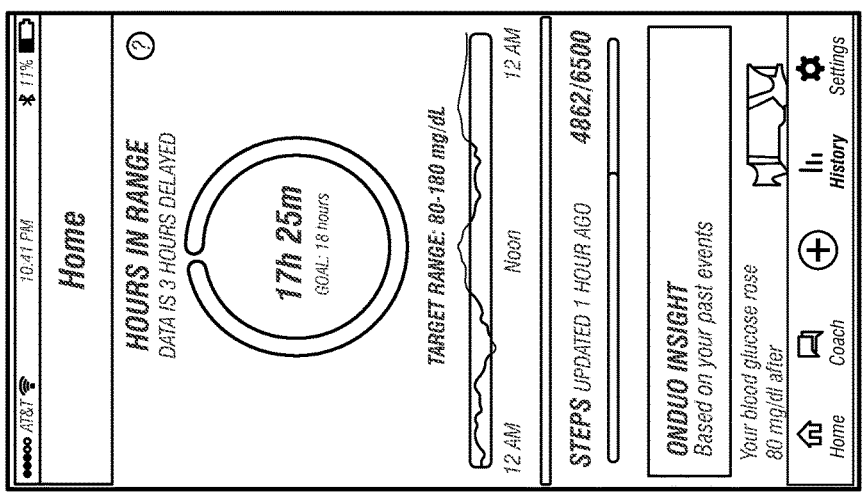
FIG. 9A depicts an example of a dashboard interface that includes a time-in-zone (TIZ) target visualization, a graphical representation of blood glucose level over time, and an indication of activity level.

FIG. 9A depicts an example of a dashboard interface that includes a TIZ target visualization, a graphical representation of blood glucose level over time, and an indication of activity level. The TIZ target visualization (here, a circular progress wheel) corresponds to a maximum value, which may be set based on the TIZ target associated with the current timeframe. Here, for example, the dynamic maximum value may dynamically vary based on Jane Doe's TIZ target for a single day. Either Jane Doe or the diabetes management platform responsible for creating the dashboard interface may modify the TIZ target.

Following the conclusion of a specified time interval, Jane Doe may be presented with an option to view a goal report. FIG. 9B depicts an example of a notification window that overlays the dashboard interface. Generally, the objective of the goal report is to allow Jane Doe to review her progress in achieving the TIZ target, specify an adjustment to the TIZ target, etc. Goal reports may be produced on a periodic basis. For example, the diabetes management platform may produce a goal report each day, week, month, etc.

Figure 9C:
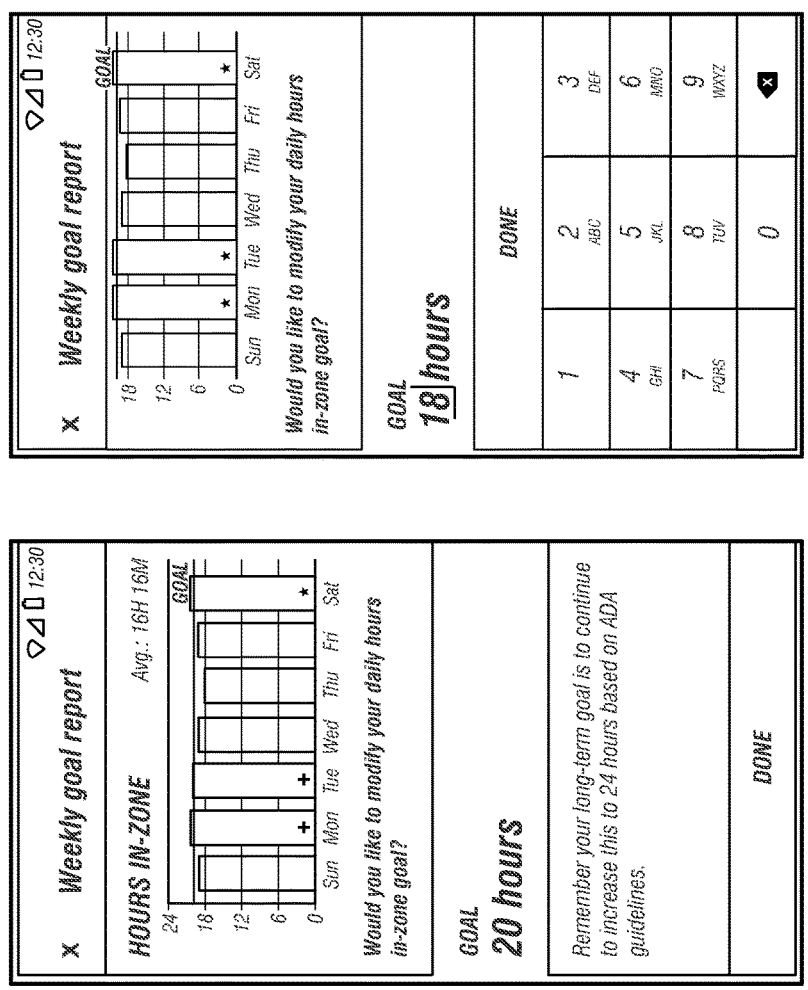
FIG. 9C depicts an example of a goal report interface that illustrates how an individual has performed over a specified time interval.

After selecting the view icon presented in the notification window, Jane Doe may be shown a goal report interface. FIG. 9C depicts an example of a goal report interface that illustrates how Jane Doe has performed over a specified time interval (here, a week). The goal report interface may also permit Jane Doe to adjust her daily TIZ target goal and/or weekly TIZ target goal.

The goal report interface can also include a graphical representation of time spent within a specified glycemic range. Visualizing TIZ targets on a per-day basis over a weeklong period allows Jane Doe to identify the day(s) she achieved the TIZ target and discover how close she was to achieving the TIZ target on those days when she was unable to achieve the TIZ target.

In some embodiments Jane Doe manually specifies the TIZ target for an upcoming time interval, while in other embodiments the diabetes management platform automatically proposes the TIZ target for the upcoming time interval. Jane Doe may be prompted to confirm the TIZ target if she chooses to specify the TIZ target (or modify the TIZ target proposed by the diabetes management platform).

Figure 9D:
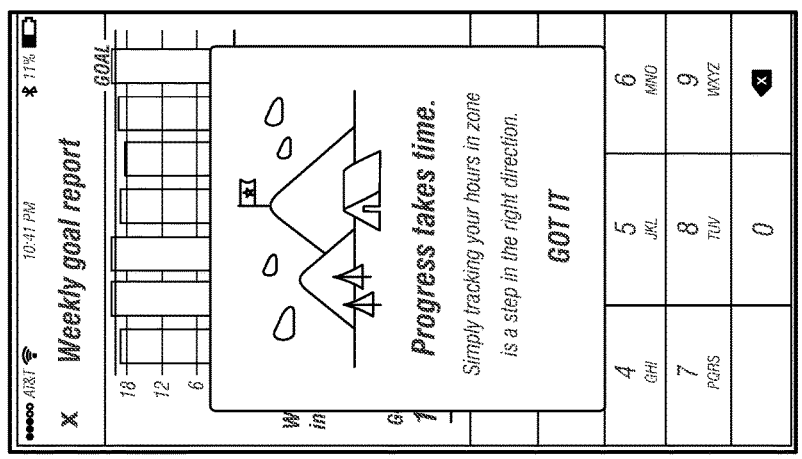
FIG. 9D depicts an example of a confirmation window that may be shown if the current TIZ target was modified to be greater than the previous TIZ target.
Figure 9E:
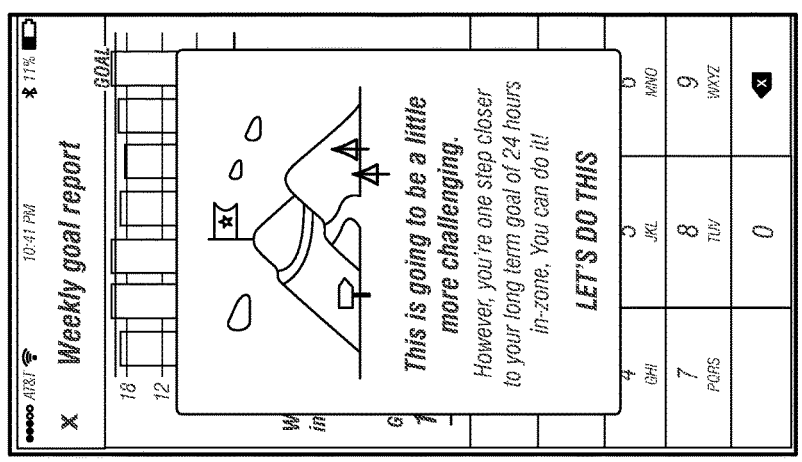
FIG. 9E depicts an example of a confirmation window that may be shown if the current TIZ target is less than or equal to the previous TIZ target.

Several different interfaces may be shown to Jane Doe based on how the TIZ target for the upcoming time interval relates to the TIZ target for the previous time interval. For example, FIG. 9D depicts an example of a confirmation window that may be shown if the current TIZ target was modified to be greater than the previous TIZ target. As another example, FIG. 9E depicts an example of a confirmation window that may be shown if the current TIZ target is less than or equal to the previous TIZ target.

Figure 9F:
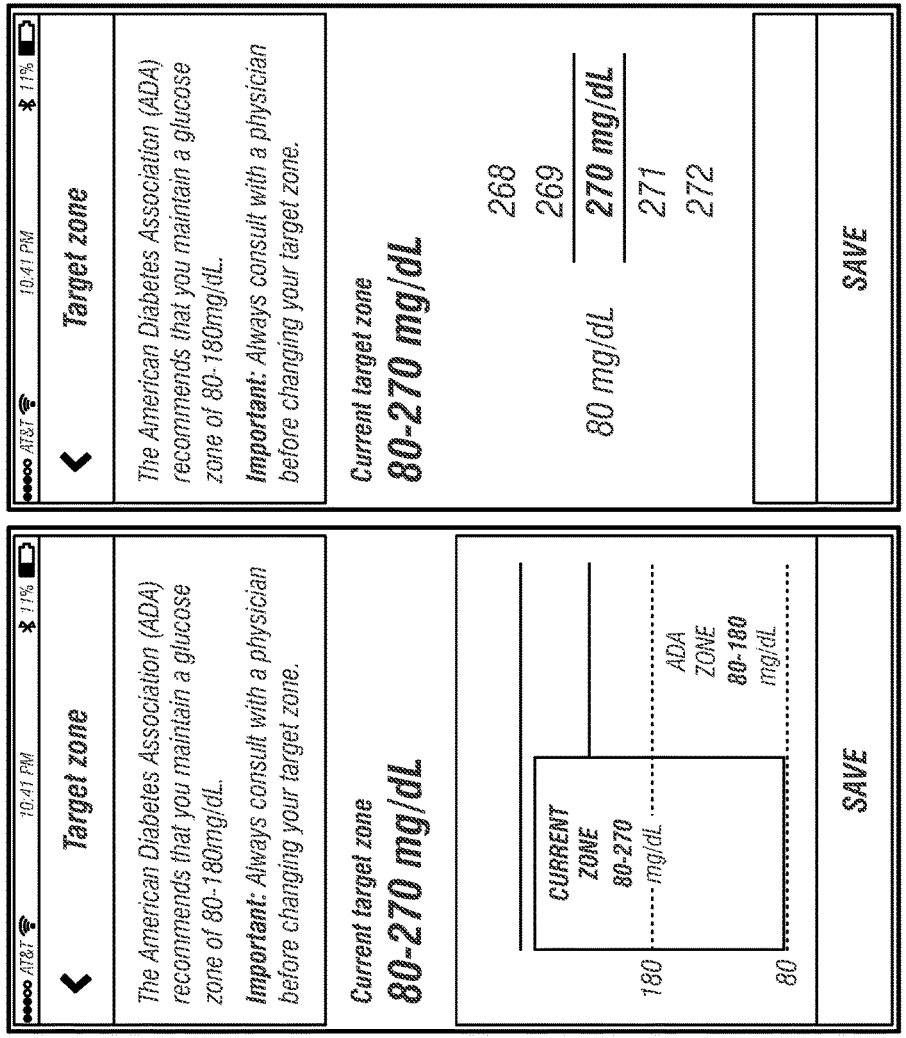
FIG. 9F depicts an example of a modification interface that may permit an individual to modify the upper bound and the lower bound of the target glycemic range.

Jane Doe may also be able to modify her target glycemic zone for a specified time interval. FIG. 9F depicts an example of a modification interface that may permit Jane Doe to modify the upper bound and the lower bound of the target glycemic range. As shown here, the modification interface may also specify the glycemic range recommended by the ADA. In some embodiments, either the upper bound or the lower bound is fixed. For example, the lower bound may be fixed to 4.4 mmol/L (80 mg/dL).

Figure 9G:
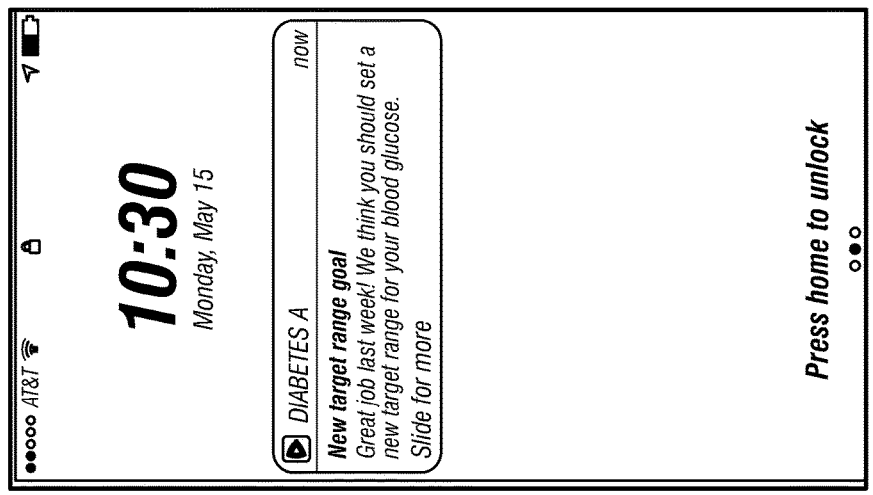
FIG. 9G depicts an example of a push notification that may be shown if a diabetes management platform determines that a new target glycemic range should be provided to an individual.
Figure 9H:
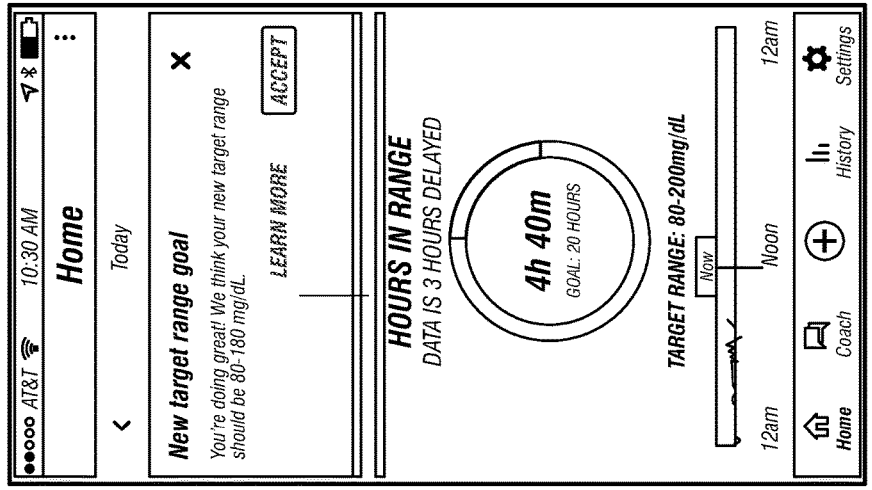
FIG. 9H depicts an example of a confirmation window that overlays the dashboard.
Figure 9I:
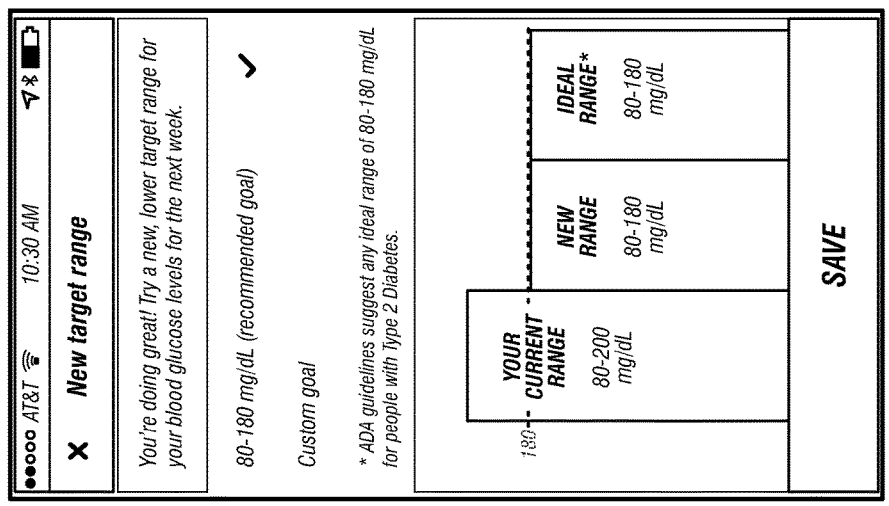
FIG. 9I depicts an example of a progression interface that may illustrate progression the individual has made toward an ideal glycemic range.

The diabetes management platform may also assist Jane Doe in reaching a glycemic range corresponding to a healthy glycemic state. FIG. 9G depicts an example of a push notification that specifies Jane Doe should set a new target glycemic range for an upcoming time interval (here, a week). The diabetes management platform may cause the push notification to be shown, for example, if the diabetes management platform determines that the individual achieved the TIZ target for the current time interval. FIG. 9H depicts an example of a confirmation window that overlays the dashboard. The confirmation window could include a proposed TIZ target, an upper bound of a target glycemic range, a lower bound of the target glycemic range, etc. The diabetes management platform may use these proposed value(s) in response to determining that Jane Doe has confirmed the proposed value(s). Additionally or alternatively, Jane Doe may manually specify these value(s) as described above. FIG. 9I, meanwhile, depicts an example of a progression interface that may illustrate progression the individual has made toward an ideal glycemic range. Together, FIGS. 9G-I can help guide Jane Doe toward the glycemic range corresponding to the healthy glycemic state in a manner more susceptible to behavior change.

Processing System

Figure 10:
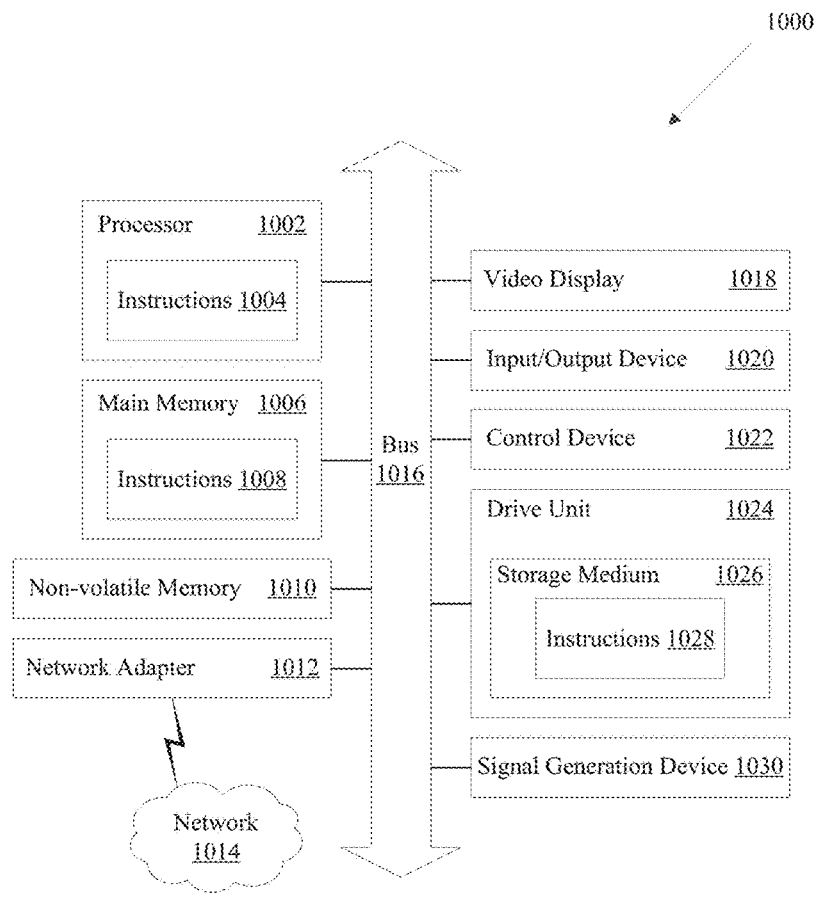
FIG. 10 is a block diagram illustrating an example of a processing system in which at least some operations described herein can be implemented.

FIG. 10 is a block diagram illustrating an example of a processing system 1000 in which at least some operations described herein can be implemented. For example, some components of the processing system 1000 may be hosted on a computing device that includes a diabetes management platform (e.g., diabetes management platform 200 of FIG. 2).

The processing system 1000 may include one or more central processing units ("processors") 1002, main memory 1006, non-volatile memory 1010, network adapter 1012 (e.g., network interface), video display 1018, input/output devices 1020, control device 1022 (e.g., keyboard and pointing devices), drive unit 1024 including a storage medium 1026, and signal generation device 1030 that are communicatively connected to a bus 1016. The bus 1016 is illustrated as an abstraction that represents one or more physical buses and/or point-to-point connections that are connected by appropriate bridges, adapters, or controllers. The bus 1016, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1000 may share a similar computer processor architecture as that of a desktop computer, tablet computer, personal digital assistant (PDA), mobile phone, game console (e.g., Sony PlayStation® or Microsoft Xbox®), music player (e.g., Apple iPod Touch®), wearable electronic device (e.g., a watch or fitness tracker), network-connected ("smart") device (e.g., a television or home assistant device), virtual/augmented reality systems (e.g., a head-mounted display such as Oculus Rift® or Microsoft Hololens®), or another electronic device capable of executing a set of instructions (sequential or otherwise) that specify action(s) to be taken by the processing system 1000.

While the main memory 1006, non-volatile memory 1010, and storage medium 1026 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1028. The term "machine-readable medium" and "storage medium" shall also be taken to include any medium that is capable of storing, encoding, or carrying a set of instructions for execution by the processing system 1000.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1004, 1008, 1028) set at various times in various memory and storage devices in a computing device. When read and executed by the one or more processors 1002, the instruction(s) cause the processing system 1000 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1010, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1012 enables the processing system 1000 to mediate data in a network 1014 with an entity that is external to the processing system 1000 through any communication protocol supported by the processing system 1000 and the external entity. The network adapter 1012 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1012 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A computer-implemented method comprising:
   configuring a patient profile with multi-tiered glycemic thresholds,
      wherein the patient profile is associated with an electronic device and a glucose monitoring device, and
      wherein a lower tier corresponds to a lower target glycemic range as compared to a higher target glycemic range that corresponds to a higher tier;
   acquiring data generated by the glucose monitoring device that monitors a blood glucose level of an individual over successive time intervals;
   for each time interval of the successive time intervals,
      calculating a time-in-range (TIR) measure indicative of a duration during which the blood glucose level was within a corresponding target glycemic range,
         wherein the corresponding target glycemic range is defined by a first upper bound and a first lower bound; and
      identifying an appropriate target glycemic range for a next time interval based at least in part on the corresponding target glycemic range,
         wherein the appropriate target glycemic range is defined by a second upper bound and a second lower bound, and
         wherein the second upper bound is lower than the first upper bound and the second lower bound is lower than the first lower bound; and
   generating a notification for presentation on a display of the electronic device,
      wherein the notification specifies a particular tier corresponding to the appropriate target glycemic range,
      wherein said generating causes the electronic device to successively present tiers corresponding to gradually lowering target glycemic ranges, and
      wherein said generating causes the individual to be guided toward a glycemic range indicative of a healthy glycemic state over time.

2. A computer-implemented method comprising:
   configuring a patient profile with multi-tiered glycemic thresholds,
      wherein the patient profile is associated with an electronic device and a glucose monitoring device;
   acquiring data generated by the glucose monitoring device that monitors a blood glucose level of an individual over a first time interval;
   calculating a time-in-range (TIR) measure indicative of a duration during which the blood glucose level was within a first glycemic range during the first time interval, wherein the first glycemic range is defined by a first upper bound and a first lower bound;
determining that the TIR measure exceeds a specified threshold;
identifying a second glycemic range based at least in part on the first glycemic range,
    wherein the second glycemic range is defined by a second upper bound and a second lower bound, and
    wherein the second upper bound is lower than the first upper bound and the second lower bound is lower than the first lower bound, and
    wherein the blood glucose level is expected to remain within the second glycemic range during a second time interval; and
causing a notification to be presented on a display of the electronic device associated with the individual,
    wherein the notification specifies that the blood glucose level is expected to remain within the second glycemic range during the second time interval,
    wherein said causing results in tiers corresponding to gradually lowering target glycemic ranges being successively presented to the individual, and
    wherein said causing results in the individual being guided toward a glycemic range indicative of a healthy glycemic state over time.

3. The computer-implemented method of claim 2, wherein the specified threshold is a predetermined percentage of the first time interval.

4. The computer-implemented method of claim 2, further comprising:
receiving input indicative of user input provided at the electronic device,
    wherein the input specifies whether a glycemic range modification is desired by the individual.

5. The computer-implemented method of claim 2, wherein the second glycemic range is based at least in part on the diabetes management success of a cohort that includes the individual.

6. The computer-implemented method of claim 5, wherein the cohort includes individuals sharing a characteristic in common, and wherein the characteristic is a combination of race, age, sex, medication program, and/or diabetes type.

7. The computer-implemented method of claim 2, wherein said configuring includes:
dynamically adjusting, based on blood glucose level history, data from the electronic device that is indicative of a contextual event involving the individual, the multi-tiered glycemic thresholds, or a combination thereof.

8. The computer-implemented method of claim 2, wherein said configuring includes:
dynamically adjusting, based on blood glucose level history, data from the electronic device that is indicative of a contextual event involving the individual, the first time interval, the second time interval, or a combination thereof.

9. The computer-implemented method of claim 8, wherein said dynamically adjusting is performed based on an adjustable parameter that is
manually specified by the individual,
manually specified by another individual, or
dynamically generated by a processor and confirmed by the individual or the other individual.

10. A computer-implemented method comprising:
acquiring, by a processor, first data generated by a glucose monitoring device that monitors a blood glucose level of an individual over a first time interval;
calculating, by the processor, a time-in-range (TIR) measure indicative of a duration during which the blood glucose level was within a first glycemic range during the first time interval,
    wherein the first glycemic range is defined by a first upper bound and a first lower bound;
determining, by the processor, that the TIR measure exceeds a specified threshold;
identifying, by the processor, a second glycemic range based at least in part on the first glycemic range,
    wherein the second glycemic range is defined by a second upper bound and a second lower bound, and
    wherein the second upper bound is lower than the first upper bound and the second lower bound is lower than the first lower bound; and
causing, by the processor, a notification to be shown by a mobile application executing on a mobile phone,
    wherein the notification specifies that the blood glucose level is expected to remain within the second glycemic range during a second time interval,
    wherein said causing results in tiers corresponding to gradually lowering target glycemic ranges being successively presented to the individual, and
    wherein said causing results in the individual being guided toward a target glycemic range indicative of a healthy glycemic state over time.

11. The computer-implemented method of claim 10, wherein the first glycemic range and the second glycemic range partially overlap.

12. The computer-implemented method of claim 10, wherein the second glycemic range is closer than the first glycemic range to the target glycemic range corresponding to the healthy glycemic state.

13. The computer-implemented method of claim 10, wherein the glucose monitoring device is selected from:
a continuous glucose monitor (CGM) that continuously monitors the blood glucose level of the individual, or
a blood glucose meter (BGM) that periodically monitors the blood glucose level of the individual.

14. The computer-implemented method of claim 10, further comprising:
acquiring, by the processor, second data generated by the glucose monitoring device that monitors the blood glucose level of the individual over the second time interval;
calculating, by the processor, another TIR measure indicative of a duration during which the blood glucose level was within the second glycemic range during the second time interval;
determining, by the processor, that the other TIR measure exceeds the specified threshold;
identifying, by the processor, a third glycemic range based at least in part on the second glycemic range,
    wherein the third glycemic range is defined by a third upper bound and a third lower bound, the third upper bound being lower than the second upper bound; and
causing, by the processor, another notification to be shown by the mobile application executing on the mobile phone,
    wherein the other notification specifies that the blood glucose level is expected to remain within the third glycemic range during a third time interval.

15. The computer-implemented method of claim 14, further comprising:

causing, by the processor, a graphical representation to be created that visually depicts directionality of the blood glucose level over time,
    wherein the graphical representation identifies the first glycemic range, the second glycemic range, and the third glycemic range.

16. The computer-implemented method of claim 14, wherein the third lower bound is lower than the second lower bound.

* * * * *